United States Patent [19]
Billet et al.

[11] 3,946,070
[45] Mar. 23, 1976

[54] PROCESS FOR THE PREPARATION OF SATURATED LONG-CHAIN DICARBOXYLIC ACIDS

[75] Inventors: Lucien Billet, Lyon; Guy Lartigau, Tassin-La-Demi-Lune, both of France

[73] Assignee: Rhone-Poulenc Textile, Paris, France

[22] Filed: July 1, 1974

[21] Appl. No.: 484,925

[30] Foreign Application Priority Data
July 3, 1973  France .............................. 73.24435

[52] U.S. Cl. .......... 260/537 P; 260/535 R; 260/540
[51] Int. Cl.² ........................................ C07C 51/16
[58] Field of Search ................................. 260/537 P

[56] References Cited
UNITED STATES PATENTS
2,601,223  6/1952  Roedel ............................ 260/537 P

*Primary Examiner*—Vivian Garner
*Attorney, Agent, or Firm*—Cushman, Darby & Cushman

[57] ABSTRACT

A process for preparing long-chain alkanedicarboxylic acids is described, starting from cycloalkanone peroxide, by double deperoxidation by means of ferrous ions in the presence of hydrogen and a hydrogenation catalyst.

26 Claims, No Drawings

PROCESS FOR THE PREPARATION OF SATURATED LONG-CHAIN DICARBOXYLIC ACIDS

The present invention relates to a process for the preparation of saturated, long chain dicarboxylic acids.

Numerous processes for the preparation of long chain dicarboxylic acids have been proposed; amongst the most valuable, there are two groups which depend on the nature of the starting product. According to a first group of processes, the long chain acid is obtained from a compound which has the same number of carbon atoms as the desired product. Thus decanedioic acid can be prepared by oxidation of cyclodecane by means of the usual oxidising agents and dodecanedioic acid can be prepared by oxidation of cyclic hydrocarbons such as cyclododecane and cyclododecene.

According to the second group of processes, the aliphatic dicarboxylic acid is prepared from cycloalkanones or cycloalkanols containing half as many carbon atoms as the desired acid, by means of a two-stage process involving firstly the formation of peroxide compounds and then the double reduction of the latter.

It is known that during the oxidation of cycloalkanones by hydrogen peroxide, various peroxides are formed, especially those corresponding to the following formulae:

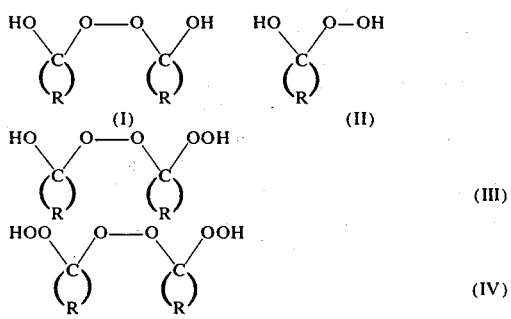

in which R represents a saturated, linear or branched divalent radical (see, for example, U.S. Pat. No. 2,298,405; N. A. MILAS et al., J. Am. Chem. Soc. 61, 2430–32 (1939); E. G. E. HAWKINS, J. Chem. Soc. 1955, 3463–67; and M. KARASH et al., J. Org. Chem., 23, 1322–26 (1958)). The distribution of these peroxides seems to vary depending on the reaction conditions, and, according to M. S. KARASH et al., loc. cit., and V. L. ANTONOVSKI, J. Appl. Chem. USSR, 40, 2443 (1967), only the peroxide of formula (I) is obtained when the oxidation of cycloalkanones is carried out in a neutral medium, and only the peroxides of formula (III) and (IV) are obtained when the reaction is carried out in the presence of inorganic acids. Although the peroxide of formula (II) has not been isolated, it has been described as the intermediate in the formation of the peroxide of formula (I) during the oxidation of cycloalkanones by $H_2O_2$ and would be in equilibrium with it and the starting cycloalkanone in crude solutions resulting from the oxidation of cycloalkanones (see V. L. ANTONOVSKI et al., Russian J. of Phys. Chem., 39, 1549–52). The same peroxide compounds can also be obtained by oxidation of cycloalkanols such as cyclohexanol and cyclopentanol, by means of oxygen in the presence or absence of a free radical initiator (see, for example, U.S. Pat. No. 2,601,223 and N. BROWN et al., J. Am. Chem. Soc., 77, 1756–59 (1955)).

It is also known that peroxides resulting from the oxidation of cycloalkanones by means of hydrogen peroxide, or resulting from the autocatalytic oxidation of cycloalkanols by means of oxygen, (both of these are referred to hereafter as "peroxides of the type of those obtained during the oxidation of cycloalkanones by means of hydrogen peroxide" or, simply, as "cycloalkanone peroxides") are decomposed to form dicarboxylic acids by reducing agents such as ions of metals which have more than one valency state and, more particularly ferrous ions, most frequently in the form of the sulphate, optionally in the presence of an inorganic acid such as sulphuric acid (see, for example, U.S. Pat. No. 2,601,223; M. S. KARASH et al., loc. cit; and E. G. E. HAWKINS loc. cit.) or a ferrous carboxylate, for example ferrous caproate, ferrous acetate or ferrous heptanoate. This reaction is preferably carried out in an organic solvent such as an alcohol, benzene, toluene, esters or ether, but it can also take place in aqueous solutions of ferrous sulphate, optionally containing sulphuric acid. During this reaction, which is hereafter referred to as "double deperoxidation," there is formed, in addition to the dicarboxylic acid containing twice as many carbon atoms as in the cycloalkanone starting material, a monocarboxylic acid containing the same number of carbon atoms as the starting material as well as cyclohexanone.

This double deperoxidation can be carried out after the cycloalkanone peroxides especially the 1,1′-dihydroxycycloalkyl peroxides have been isolated but it is more convenient to use the crude solution resulting from the oxidation of the cycloalkanone or the cycloalkanol. It is then preferable to use the same solvent for the oxidation step as for the double deperoxidation step, particularly in the case of the oxidation of cyaloalkanones by means of hydrogen peroxide.

Double deperoxidation of cycloalkanone peroxides is an attractive method for preparing long chain dicarboxylic acids such as 1,10-decanedioic acid, 1,12-dodecanedioic acid and 4,9-dimethyl-1,12-dodecanedioic acid, which are important industrial products, especially for the preparation of polycondensates of the linear polyester and polyamide type intended for manufacturing textile fibres, because the starting cycloalkanones and cycloalkanols are common, relatively inexpensive products. However, the regeneration of ferrous ions from the ferric ions formed during the deperoxidation has proved to be one of the obstacles to the industrial application of such a process. In fact, no matter what the deperoxidation agent, the solvent used and the origin and the nature of the peroxide subjected to deperoxidation may be, the amount of ferrous ions employed should represent at least one ferrous ion per atom of active oxygen present in the peroxide material employed in the reaction. During this reaction, the ferrous ions are converted to ferric ions. For economic reasons and to avoid discharging large amounts of effluent containing ferric ions, it is thus important to regenerate ferrous ions from ferric ions so that they can be recycled to the deperoxidation process.

The present invention proposes to solve the problem posed by the regeneration of ferrous ions during the process of effecting deperoxidation of peroxides of the type of those obtained by oxidation of cycloalkanones by means of hydrogen peroxide. More specifically, the present invention provides a process for the preparation of a linear or branched alkanedicarboxylic acid possessing at least 8 carbon atoms in the linear divalent chain separating the two hydroxycarbonyl groups, by double deperoxidation by means of ferrous ions, in a suitable solvent, of peroxides of the type obtained by oxidation of cycloalkanones by means of hydrogen peroxide, characterised in that the reaction is carried out in the presence of hydrogen and a hydrogenation catalyst.

The cycloalkanone peroxides amenable to the deperoxidation process according to the invention can have been prepared by any one of the processes mentioned above.

Thus, in order to carry out the double deperoxidation process according to the invention, it is possible to use one of the peroxides or a mixture of two or more of the peroxides obtained during the oxidation, by means of hydrogen peroxide, of cycloalkanones of the general formula:

(V)

or during the self-oxidation of cycloalkanols of the general formula:

(VI)

in which R represents a linear saturated divalent hydrocarbon radical containing 5 to 8 carbon atoms, optionally substituted by 1 to 3 alkyl radicals containing 1 to 4 carbon atoms; they can be isolated beforehand from the medium in which they were prepared or, preferably, are in the form of solutions in the crude reaction mixtures resulting from the oxidation of cycloalkanones and cycloalkanols. Amongst these peroxides, those of formula (I), alone or mixed with peroxides of the formula (II) and/or (III) and/or (IV) in which R is as defined above, are preferably used.

Examples of cycloalkanones which can be oxidised by means of hydrogen peroxide to yield the peroxides which can be used in the present invention, include cyclopentanone, cyclohexanone, 2-methyl-cyclohexanone, 3-methyl-cyclohexanone, 4-methyl-cyclohexanone, cycloheptanone and cyclooctanone. Cyclopentanol and cyclohexanol are examples of cycloalkanols of formula (VI).

Amongst the peroxides of formula (I), there may be mentioned, especially, 1,1'-dihydroxy-cyclohexyl peroxide; 1,1'-dihydroxy-cyclopentyl peroxide; 1,1'-dihydroxy-2,2'-dimethyl-cyclohexyl peroxide; 1,1'-dihydroxy-3,3'-dimethylcyclohexyl peroxide; 1,1'-dihydroxy-cycloheptyl peroxide; and 1,1'-dihydroxy-cyclooctylperoxide.

The double deperoxidation process can be carried out in the organic solvents usually employed, such as saturated aliphatic alcohols, especially those possessing 1 to 4 carbon atoms, such as methanol, ethanol or propanol, aromatic hydrocarbons, such as benzene, and esters or ethers, for example ethyl ether and dioxane, and in the presence of ferrous ions such as ferrous salts of inorganic acids, especially ferrous sulphate, or ferrous salts of carboxylic acids, or in aqueous acid solutions of ferrous sulphate. The process of this invention can also be used when carboxylic acids are used as the solvent and ferrous carboxylates are used as the deperoxidation agent. In fact, it has been found that it is particularly advantageous to prepare long chain dicarboxylic acids:

a. by double deperoxidation of cycloalkanone peroxides, especially those of general formula (I), individually or mixed with peroxides of the general formulae (II) and/or (III) and/or (IV), prepared by any one of the abovementioned processes (and then isolated), by carrying out the deperoxidation in a saturated aliphatic carboxylic acid possessing at least two carbon atoms and preferably at most 12 carbon atoms, for example, acetic acid, propionic acid, butyric acid, pentanoic acid, caproic acid, heptanoic acid or octanoic acid, by means of ferrous carboxylates, for example ferrous acetate, ferrous propionate, ferrous butyrate, ferrous pentanoate, ferrous caproate, ferrous heptanoate, ferrous octanoate, ferrous resinate, ferrous naphthenate or ferrous benzoate. The carboxylate corresponding to the acid solvent is generally chosen.

b. by double deperoxidation, by means of ferrous carboxylates, of the oxidised products resulting from the oxidation, by means of hydrogen peroxide, of cycloalkanones of formula (V) in a saturated carboxylic acid possessing at least two carbon atoms and preferably at most 12 carbon atoms.

As the carboxylic acid, that which is formed during the deperoxidation is generally used, for example caproic acid for the deperoxidation of cyclohexanone peroxides (and, where appropriate, for the oxidation of cyclohexanone by hydrogen peroxide). The oxidation of cycloalkanones by means of hydrogen peroxide in carboxylic acids, (which does not form part of the present invention) can be carried out under the usual conditions for known processes (see, for example U.S. Pat. No. 2,298,405).

In addition to the advantage arising from the continuous regeneration in situ of ferrous ions from ferric ions, the double deperoxidation process under hydrogen makes it possible to use amounts of ferrous salts which are very much less than the stoichiometric amount and which can be as low as $10^{-3}$ ferrous ion per atom of active oxygen of peroxide preferably from $10^{-2}$ to 0.75 ferrous ion per atom of peroxide oxygen; this represents a considerable economic advantage. Another advantage results from the following possibility: in order to ensure that the reaction takes place satisfactorily, it is in fact necessary for the ferrous salts used to be dissolved in the solvents employed, and, because of the low solubility of ferrous salts in organic solvents, this involves the use of very large quantities of the latter, and this has led to a lowering of the productivity of the equipment. On the other hand, the use of small amounts of ferrous salts, which is possible with the process of this invention, makes it possible to reduce considerably the volume of solvent employed in the double deperoxidation process and consequently to increase the productivity of the equipment. Of course, this invention is not limited to the use of amounts of ferrous ions lying within the limits defined above, these limits being preferred only. The use of amounts of ferrous ions substantially equal to or greater than the stoichiometric amount, for example, 2.5 ferrous ions per atom of active oxygen, is still possible. In short, the process of this invention can generally be carried out with quantities of ferrous ions of from $10^{-3}$ to 2.5 ferrous ions per atom of active oxygen.

Preferred hydrogenation catalysts for use in the process of this invention are based on platinum, palladium or nickel. Although any of these catalysts can be used, it has been found that it is preferable to work in the presence of a catalyst based on platinum or palladium when the ferrous salt is derived from an inorganic acid (for example ferrous sulphate) or when the deperoxidation is carried out in an aqueous acid medium. On the other hand, nickel is particularly suitable when the deperoxidation is carried out in an organic solvent, for example an aromatic hydrocarbon in the presence of a ferrous carboxylate; it enables the ferric ions to be reduced rapidly as they are formed.

The amount of metal employed as the catalyst can generally vary from 0.001% to 10% by weight, preferably from 0.01% to 5% by weight, relative to the reaction mixture. The metal can be used alone or can be deposited on an inert support such as a carbon black, alumina, pumice stone or an active earth. It is possible, for example, to use palladium or platinum on active charcoal or to use Raney nickel.

The double deperoxidation according to the invention can be carried out under the usual conditions, for example those proposed in U.S. Pat. No. 2,601,223. Thus the reaction temperature can generally be from $-100°$ to $+100°C$, preferably from $0°$ to $100°C$. The absolute pressure of hydrogen is suitably from 0.01 to 100 bars; however, it is usually not necessary to exceed a hydrogen pressure of 50 bars. The reaction pressure and temperature are generally chosen depending on the catalyst used so as to ensure that the ferric ions are reduced rapidly, without in any way causing hydrogenation of the carboxylic acid groups and of the cycloalkanones formed. However, if the starting material used to prepare the peroxides is a cycloalkanol, it is possible, without disadvantage, to choose conditions which make it possible simultaneously to hydrogenate the cycloalkanones formed to yield cycloalkanols which can be conveyed back, after isolation, to the oxidation zone. In every case, the optimum conditions can be determined by means of simple tests.

The double deperoxidation by ferrous ions in the presence of hydrogen can be carried out in accordance with the usual methods for ensuring contact between a gas and a liquid in the presence of a solid. For example, the liquid phase containing the catalyst in suspension can be passed continuously through a suitably equipped column, for example a column with a packing or a column with plates, in co-current or counter-current with a hydrogen flow. The process according to the present invention is particularly suitable for continuous operation.

The following Examples further illustrate the present invention.

EXAMPLE 1

26.5 g of a solution of ferrous hexanoate in hexanoic acid containing 0.75 gram atom of iron per kilogram of solution (that is to say 0.02 gram atom) and 1.4 cm$^3$ of Raney nickel are introduced, under a nitrogen atmosphere, into a 250 cm$^3$ glass flask which is equipped with a thermometer, a dropping funnel, a stirring system and a dip tube for introducing gas and which is cooled by a bath of cold water; the apparatus is then purged with hydrogen, and a reaction mixture which is produced by reacting: 9.8 g of cyclohexanone (0.1 mol), 2.57 of 67% by weight hydrogen peroxide (0.0505 mol) and 20 cm$^3$ of hexanoic acid at 20°C for 5 minutes, and which consists of an equilibrium mixture of 1-hydroxy-cyclohexyl hydroperoxide, 1,1'-dihydroxy-cyclohexyl peroxide and cyclohexanone, is introduced over the course of 3 hours 40 minutes into the flask cooled to 20°C, under a relative hydrogen pressure of 30 cm of water. The ratio of the number of gram atoms of ferrous ion to the number of atoms of active oxygen is 0.39.

A portion of the dodecanedioic acid formed precipitates during the reaction; at the end of the reaction, the reaction mixture is filtered in order to isolate the precipitate and the catalyst and the whole is washed on the filter with 50 g of tetrahydrofurane in order to extract the acid; in this way, 107.5 g of a solution are obtained, in which the following constituents are measured by gas/liquid chromatography (after forming the methyl esters of the acids present):

| | |
|---|---|
| cyclohexanone: | 5.6 g |
| cyclohexanol: | 0.05 g |
| 2-n-butyl-octanedioic acid: | 0.115 g |
| dodecanedioic acid: | 3.26 g | corresponding to a yield of dodecanedioic acid of 67% relative to the cyclohexanone converted and 56% relative to the active oxygen.

The total volume of hydrogen absorbed, measured at normal pressure and temperature, is 0.730 liter.

At the end of the reaction, 0.02 gram atom of ferrous ion is measured in the reaction mixture.

EXAMPLE 2

The process is carried out in the apparatus and in accordance with the procedure described in Example 1, replacing the ferrous hexanoate by ferrous pentanoate and the hexanoic acid by pentanoic acid. The amounts of reagents and the conditions are as follows:

| | |
|---|---|
| solution of ferrous pentanoate in pentanoic acid containing 0.79 gram atom of iron/kg: | 22.6 g |
| Raney nickel: | 1.4 cm$^3$ |
| peroxide solution produced as in Example 1, but in pentanoic acid | |
| time taken to add the peroxide solution: | 2 h 30 m |
| temperature: | 15°C |
| hydrogen pressure: | 30 cm of water |
| iron/active oxygen ratio: | 0.35 |

After filtering off the precipitate and washing it with tetrahydrofurane, 90.9 g of a solution are recovered, in which the following constituents are measured by gas/liquid chromatography:

| | |
|---|---|
| cyclohexanone: | 5.15 g |
| cyclohexanol: | 0.05 g |
| hexanoic acid: | 1.5 g |
| 2-n-butyl-octanedioic acid: | 0.115 g |
| dodecanedioic acid: | 3.72 g |

The yield of dodecanedioic acid is 64% relative to the active oxygen and 69% relative to the cyclohexanone converted.

The total volume of hydrogen absorbed, measured at normal pressure and temperature, is 0.740 liter.

0.0178 gram atom of ferrous ion is measured at the end of the reaction, corresponding to 100% of the ferrous ion introduced.

EXAMPLE 3

The same procedure as in Example 2 is used, with the following amounts of reagents:

| | |
|---|---|
| solution of ferrous pentanoate in pentanoic acid of Example 2: | 23.4 g |
| Raney nickel: | 1.4 cm³ |
| peroxide solution prepared as in Example 1 from: | |
| cyclohexanone: | 29 g |
| 67% by weight H₂O₂ | 7.5 g |
| pentanoic acid | 80 g |

The reaction conditions were as follows:

| | |
|---|---|
| temperature: | 15°C |
| time taken to add the peroxide solution: | 6 h 25 m |
| H₂ pressure: | 30 cm of water |
| iron/active oxygen ratio: | 0.125 |

After filtration and washing the cake with 115 cm³ of tetrahydrofurane, 221 g of a solution are recovered, in which the following constituents are measured:

| | | |
|---|---|---|
| cyclohexanone: | 16.1 | g |
| cyclohexanol: | 0.12 | g |
| hexanoic acid: | 4.6 | g |
| 2-n-butyl-octanedioic acid: | 0.36 | g |
| dodecanedioic acid: | 9.2 | g |

The yield of dodecanedioic acid is 55% relative to the active oxygen and 62% relative to the cyclohexanone converted.

The total volume of hydrogen absorbed is 2.020 liters and, at the end of the reaction, 0.0185 gram atom of ferrous ion is measured in the reaction mixture, corresponding to 100% of the ferrous ion introduced.

EXAMPLE 4

The same procedure as in the preceding Examples is used, with the following amounts of reagents:

| | |
|---|---|
| solution of ferrous pentanoate in pentanoic acid containing 1.25 gram atom of iron kg: | 16 g |
| Raney nickel: | 1.4 cm³ |
| peroxide solution obtained as in Example 1 from: | |
| cyclohexanone: | 78 g |
| 67% by weight H₂O₂ | 20 g |
| pentanoic acid: | 210 g |

The reaction conditions are those of Example 3, except for the time taken to add the peroxide solution which is 10 hours 30 minutes, and the iron/active oxygen ratio which is 0.050.

During the reaction, a precipitate forms which is filtered off and then washed with 300 cm³ of benzene; 603.9 g of a solution are recovered, in which the following constituents are measured:

| | | |
|---|---|---|
| cyclohexanone: | 42.2 | g |
| cyclohexanol: | 0.4 | g |
| hexanoic acid: | 16 | g |
| 2-n-butyl-octanedioic acid: | 1.15 | g |
| dodecanedioic acid: | 7.57 | g |

The cake, which has been isolated beforehand and which contains the catalyst and dodecanedioic acid is washed with 170 cm³ of tetrahydrofurane. In this way, 164.9 g of a solution are obtained, in which 11.2 g of dodecanedioic acid are measured.

The total yield of this acid is 41% relative to the active oxygen and 45% relative to the cyclohexanone converted.

The total volume of hydrogen absorbed is 5.5 liters and the amount of ferrous ion present in the reaction medium is 0.020 gram atom.

EXAMPLE 5

The same procedure as in the preceding Examples is used, with the following amounts of reagents:

| | |
|---|---|
| Solution of ferrous pentanoate in pentanoic acid containing 1.015 gram atoms of iron/kg: | 43.5 g |
| Raney nickel: | 3.7 cm³ |

Peroxide solution obtained as in the preceding Examples from:

| | |
|---|---|
| cyclohexanone: | 9.8 g |
| 68% by weight H₂O₂ | 2.52 g |
| pentanoic acid: | 20 cm³ |

The reaction conditions are those of Example 4 except for the time taken for the running-in which is 3 hours 10 minutes and the iron/active oxygen ratio which is 0.9.

After filtration and washing the catalyst with 50 cm³ of tetrahydrofurane, 141.4 g of a solution are obtained, in which the following constituents are measured:

| | |
|---|---|
| Cyclohexanone: | 5 g |
| Cyclohexanol: | 0.04 g |
| Hexanoic acid: | 1.18 g |
| n-Butyl-octanedioic acid: | traces |
| Dodecanedioic acid: | 3.77 g |

The yield of this acid is 65.5% relative to the active oxygen and 67% relative to the cyclohexanone consumed.

The volume of hydrogen absorbed is 0.75 liter and the amount of ferrous ion measured at the end of the reaction is 0.044 gram atom.

EXAMPLE 6

The following constituents are introduced, under a nitrogen atmosphere, into the apparatus described in Example 1:

| | |
|---|---|
| FeSO₄. 7H₂O: | 2.9 g |
| 98% by weight H₂SO₄: | 2.04 g |
| Methanol: | 40 cm³ |
| Platinum on carbon black containing 5% by weight of metal: | 27 mg |

The apparatus is then purged with hydrogen, its contents are cooled to 10°C, and a hydrogen pressure of 30 cm of water is then established. A peroxide solution which was produced by reacting: 15.7 g of cyclohexanone and 3.96 g of 69% by weight H₂O₂ in 20 cm³ of methanol at 20°C for 5 minutes and which was thereafter diluted to 40 cm³ by adding methanol, is then added over the course of 5 hours 30 minutes. The iron/active oxygen ratio is 0.130.

When the addition is complete, the catalyst is filtered off and washed with 5 cm³ of methanol. In this way, 82.8 g of a solution are obtained; the following constituents are measured by gas/liquid chromatography:

| | |
|---|---|
| Cyclohexanone: | 8.15 g |
| Cyclohexanol: | 0.06 g |
| Hexanoic acid: | 2.62 g |
| 6-hydroxy-hexanoic acid: | 0.09 g |
| 2-n-butyl-octanedioic acid: | 0.83 g |
| Dodecanedioic acid: | 3.2 g |

The yield of dodecanedioic acid is 35% relative to the active oxygen and 36.5% relative to the cyclohexanone converted.

The total volume of hydrogen absorbed rises to 0.930 liter. At the end of the reaction, 0.0104 gram atom of ferrous ion is measured in the reaction medium.

EXAMPLE 7

The procedure of Example 6 is followed, introducing the same amount of the peroxide solution, over the course of 5 hours 10 minutes, into:

5.6 g of $FeSO_4.7H_2O$
2.9 g of 98% $H_2SO_4$
50 cm³ of methanol and
35 mg of platinum on carbon black containing 5% of metal (corresponding to 1.75 mg of Pt).

The iron/active oxygen ratio is 0.25. After treating the reaction mixture as in Example 6, 114.4 g of a solution are obtained, in which the following constituents are measured:

| | |
|---|---|
| Cyclohexanone: | 7.95 g |
| Cyclohexanol: | 0.06 g |
| Hexanoic acid: | 1.98 g |
| 2-n-butyl-octanedioic acid: | 0.29 |
| Dodecanedioic acid: | 5.15 g |

The yields, relative to the active oxygen and to the cyclohexanone converted, are 56%.

The total volume of hydrogen absorbed, measured at normal pressure and temperature, is 0.93 liter. At the end of the reaction, 0.020 gram atom of ferrous ion was measured in the reaction medium.

We claim:

1. In a process for the preparation of a linear or branched alkane-dicarboxylic acid possessing at least 8 chain carbon atoms separating the two hydroxycarbonyl groups, which comprises subjecting a cycloalkanone peroxide to double deperoxidation, by means of ferrous ions, the improvement wherein the double deperoxidation by means of ferrous ions is carried out in the presence of hydrogen and a metal hydrogenation catalyst selected from the group consisting of platinum, palladium and nickel.

2. Process according to claim 1, in which the catalyst is present in an amount from 0.001% to 10% by weight of the reaction mixture.

3. Process according to claim 1, in which the reaction is carried out in an organic solvent.

4. Process according to claim 3, in which the solvent is selected from a saturated aliphatic alcohol, a saturated aliphatic carboxylic acid containing 2 to 12 carbon atoms and an aromatic hydrocarbon.

5. Process according to claim 4, in which the carboxylic acid used as solvent corresponds to that which is formed as a by-product of the reaction.

6. Process according to claim 1, in which the ferrous ions are present in the form of a salt of an inorganic acid or of a carboxylic acid.

7. Process according to claim 6, in which the ferrous ions are present as ferrous sulphate.

8. Process according to claim 7, which is carried out in an aqueous acid solution of ferrous sulphate.

9. Process according to claim 6, in which the ferrous ions are present as ferrous acetate, ferrous propionate, ferrous butyrate, ferrous pentanoate, ferrous caproate, ferrous heptanoate, ferrous octanoate, ferrous resinate, ferrous naphthenate or ferrous benzoate.

10. Process according to claim 6, in which the ferrous ions are present as ferrous carboxylate derived from the carboxylic acid used as solvent.

11. Process according to claim 1, in which the reaction is carried out at a temperature of from −100° to +100°C.

12. Process according to claim 11, in which the reaction temperature is from 0° to 100°C.

13. Process according to claim 1, in which the absolute pressure of hydrogen is from 0.01 to 100 bars.

14. Process according to claim 13, in which the absolute pressure of hydrogen is from 0.01 to 50 bars.

15. Process according to claim 1, in which the ferrous ions are present in an amount from $10^{-3}$ to 2.5 ferrous ions per atom of active peroxide oxygen.

16. Process according to claim 15, in which the ferrous ions are present in an amount from $10^{-2}$ to 0.75 ferrous ions per atom of peroxide oxygen.

17. Process according to claim 1, in which the peroxide is one or more of the peroxides of the general formula:

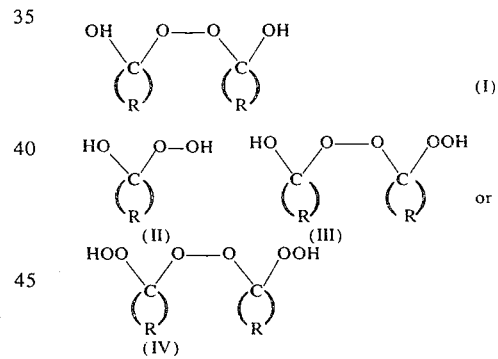

in which R represent a linear saturated divalent hydrocarbon radical possessing 5 to 8 carbon atoms, optionally substituted by 1 to 3 radicals possessing 1 to 4 carbon atoms.

18. Process according to claim 17, in which the peroxide is selected from a peroxide of formula (I) and mixtures of peroxide of formula (I) with a peroxide of one or more of formulae (II), (III) and (IV).

19. Process according to claim 17, in which the peroxide is prepared by oxidation, by means of oxygen or oxygen-containing gas, of a cycloalkanol of the general formula:

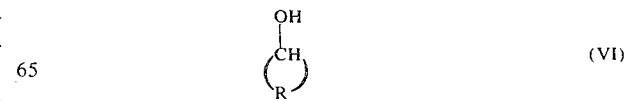

in which R is as defined in claim 17.

20. Process according to claim 17, in which the peroxide is used in solution in the crude reaction mixtures resulting from the oxidation of cycloalkanones of cycloalkanols.

21. Process according to claim 17, in which the peroxide is produced by oxidation, by means of hydrogen peroxide, of a cycloalkanone of the general formula:

  (V)

in which R is as defined in claim 17.

22. Process according to claim 21, in which the peroxide is used in the form of a crude solution resulting from the oxidation of a cycloalkanone of formula (V) by means of hydrogen peroxide in a saturated aliphatic carboxylic acid possessing 2 to 12 carbon atoms.

23. Process according to claim 21, in which the peroxide is used in the form of a crude solution resulting from the oxidation of a cycloalkanone of the formula (V) by means of hydrogen peroxide in a saturated aliphatic carboxylic acid corresponding to that which is formed during the double deperoxidation.

24. Process according to claim 1, in which the peroxide is selected from 1,1'-dihydroxy-cyclopentyl peroxide, 1,1'-dihydroxy-cyclohexyl peroxide, 1,1'-dihydroxy-2,2'-dimethyl-cyclohexyl peroxide, 1,1'-dihydroxy-3,3'-dimethyl-cyclohexyl peroxide, 1,1'-dihydroxy-4,4'-dimethyl-cyclohexyl peroxide, 1,1'-dihydroxy-cycloheptyl peroxide and 1,1'-dihydroxy-cyclooctyl peroxide.

25. Process for the preparation of 1,12-dodecanedioic acid according to claim 1, which comprises subjecting a solution of 1,1'-dihydroxy-cyclohexyl peroxide, used alone or together with one or more of 1-hydroperoxy-cyclohexanol, 1-hydroxy-1'-hydroperoxy-cyclohexyl peroxide and 1,1'-dihydroperoxycyclohexyl peroxide, in pentanoic acid, caproic acid, heptanoic acid or octanoic acid, to double deperoxidation in the presence of the ferrous salt of the acid used, hydrogen and a nickel metal catalyst.

26. Process for the preparation of 1,12-dodecanedioic acid according to claim 1, which comprises treating the crude reaction solution obtained by oxidation of cyclohexanone by means of hydrogen peroxide in a saturated aliphatic carboxylic acid with a ferrous carboxylate in the presence of hydrogen and a nickel metal catalyst.

* * * * *